US011350869B2

(12) United States Patent
Rasmussen et al.

(10) Patent No.: US 11,350,869 B2
(45) Date of Patent: Jun. 7, 2022

(54) ELECTROCARDIOGRAM (ECG) MEASUREMENT ON A WRIST-WORN ELECTRONIC DEVICE

(71) Applicant: Garmin Switzerland GmbH, Schaffhausen (CH)

(72) Inventors: Adam B. Rasmussen, Overland Park, KS (US); Kevin M. Hansen, Overland Park, KS (US); Alexander J. Waller, Olathe, KS (US)

(73) Assignee: Garmin Switzerland GmbH

( * ) Notice: Subject to any disclaimer, the term of this patent is extended or adjusted under 35 U.S.C. 154(b) by 206 days.

(21) Appl. No.: 15/686,804

(22) Filed: Aug. 25, 2017

(65) Prior Publication Data
US 2019/0059756 A1    Feb. 28, 2019

(51) Int. Cl.
*A61B 5/332* (2021.01)
*A61B 5/00* (2006.01)
(Continued)

(52) U.S. Cl.
CPC .............. *A61B 5/332* (2021.01); *A61B 5/002* (2013.01); *A61B 5/0006* (2013.01); *A61B 5/02416* (2013.01); *A61B 5/02438* (2013.01); *A61B 5/282* (2021.01); *A61B 5/339* (2021.01); *A61B 5/681* (2013.01); *A61B 5/7225* (2013.01);
(Continued)

(58) Field of Classification Search
CPC ..... A61B 5/0404; A61B 5/7225; A61B 5/006; A61B 5/02438; A61B 5/681; A61B 5/02416; A61B 5/04085; A61B 5/02427; A61B 5/0022
See application file for complete search history.

(56) References Cited

U.S. PATENT DOCUMENTS

2009/0312655 A1* 12/2009 Lo .................. A61B 5/681
600/503
2017/0119255 A1* 5/2017 Mahajan ............ A61B 7/04
(Continued)

OTHER PUBLICATIONS

Printout from https://www.alivecor.com/kardiaband/ dated prior to Aug. 25, 2017.
(Continued)

*Primary Examiner* — Mallika D Fairchild
*Assistant Examiner* — Minh Duc G Pham
(74) *Attorney, Agent, or Firm* — Samuel M. Korte; Max M. Ali

(57) ABSTRACT

An electronic device worn, such as a wrist-worn watch, able to generate and display an ECG image associated with the wearer's heart. The device includes electrically-conductive first and second contact points for conveying first and second signals. The first contact point is located on a bezel or a pushbutton of the electronic device that is physically touchable by the wearer. The second contact point is located on the bottom of the housing so as to physically contact the wearer's skin of the user's wrist when the device is worn. The electronic device may also receive location signals to determine a current location using an antenna at least partially formed by the bezel. A processing element may receive the first and second signals, generate an ECG waveform, and an ECG image based thereon. A display graphically presents the ECG image as a sequence or stream of ECG images.

30 Claims, 8 Drawing Sheets

(51) Int. Cl.
*A61B 5/024* (2006.01)
*A61B 5/282* (2021.01)
*A61B 5/339* (2021.01)

(52) U.S. Cl.
CPC ......... *A61B 5/0022* (2013.01); *A61B 5/02427* (2013.01); *A61B 2503/10* (2013.01); *A61B 2505/09* (2013.01); *A61B 2560/0468* (2013.01)

(56) References Cited

U.S. PATENT DOCUMENTS

2017/0179581 A1* 6/2017 Puuri .................... H01Q 7/005
2017/0181644 A1* 6/2017 Meer .................. A61B 5/02438
2018/0235542 A1* 8/2018 Yun ..................... A61B 5/0205

OTHER PUBLICATIONS

Printout from http://download.nautilus.com/supportdocs/om/bowflex/bowflexfittrainerplus.pdf dated prior to Aug. 25, 2017.
Printout from http://lifetrakusa.com/wp-content/uploads/LT_300_QuickStarter-Guide_022814-English_PRiNT.pdf dated prior to Aug. 25, 2017.
Printout from http://lifetrakusa.com/wp-content/uploads/LT_R450_OS-Guide_082614-English.pdf dated prior to Aug. 25, 2017.
Printout from http://www.pulseoximeter.org/fl500_html dated prior to Aug. 25, 2017.

* cited by examiner

ELECTROCARDIOGRAM (ECG) MEASUREMENT ON A WRIST-WORN ELECTRONIC DEVICE

BACKGROUND

Wrist-worn electronic devices often include functionality that may be used to determine and track a current location of the electronic device as well as a distance traveled, a velocity, and other performance metrics or data determined using location information. This functionality may involve the electronic device receiving positional information from a satellite-based positioning system, such as the global positioning system (GPS). The electronic devices may include a location determining element and one or more antennas to receive signals from GPS satellites and provide wireless communication. Typically, the wrist-worn electronic devices also include a watch housing enclosing a processing element and a display, which is surrounded by a watch bezel. In some cases, the one or more antennas coupled to the location determining element and wireless receivers may be incorporated into the watch bezel or a portion thereof.

Electrocardiogram signals may be sensed by conventional sensory equipment having at least two sensors. The sensors are commonly placed on each side of an individual's chest to sense the electrocardiogram signals. For instance, the conventional sensory equipment may be a chest strap having two electrodes (sensors) positioned on an inner surface of the chest strap enabling the electrodes to contact the individual's chest. When the chest strap is worn, each electrode is typically positioned to contact one side of the individual's chest (separated by the sternum) such that a first electrode is positioned to contact the left side of the individual's chest and a second electrode is positioned to contact the right side of the individual's chest. The conventional sensory equipment may also be a cardiovascular monitoring device having two electrodes (sensors) and electrical wiring coupling each electrode to the cardiovascular monitoring device. An inner surface of each electrode may be secured to desires areas of an individual, such as each side of the individual's chest, using adhesive tape to sense electrocardiogram signals from the individual's heart.

The conventional sensory equipment includes wrist-worn electronic devices having two or more sensors utilized to sense electrocardiogram signals without use of a chest strap. Specifically, some conventional wrist-worn electronic devices includes a conductive contact point, such as a metal plate, on the rear surface of the watch and a dedicated conductive contact point on an exterior surface. For example, the conductive contact point on the exterior surface may be a pushbutton composed of an electrically conductive material positioned on a top surface or a side surface of the wrist-worn electronic devices. Similarly, the conductive contact point (e.g., metal plate, pushbutton, etc.) may be located between a display and a strap securing the electronic device to a user's wrist. Some conventional wrist-worn electronic devices include two conductive contact points by positioning a first conductive contact point on the exterior surface between a display and a first strap and a second conductive contact point between the display and a second strap, such that a user may simultaneously place two fingers on the conductive contact point located on an exterior surface of the electronic device.

Individuals engaged in fitness activities without use of the abovementioned conventional sensory equipment that may be uncomfortable or impractical while engaged in the fitness activities. The individuals may desire to obtain or monitor cardiovascular information, such their heart rate, or other cardiac parameters for use to reach their fitness and cardiovascular objectives while engaged in the fitness activities.

SUMMARY

Embodiments of the present technology provide an electronic fitness device configured to generate and graphically display one or more electrocardiogram images associated with an electrocardiogram waveform of a wearer's heart. The electronic device may utilize two contact points to receive electrical bio signals (electrocardiogram signals) from the wearer, from which a processing element may generate the electrocardiogram waveform. A first contact point may be located on a watch bezel or a depressible pushbutton that is physically contacted by a finger or thumb of the wearer. A second contact point may be located on an underside of the electronic device where it may be in generally constant contact with the wearer's skin of the wearer's wrist.

In an embodiment, a wrist-worn electronic fitness device may comprise a housing, an electrically-conductive plate, an electrically-conductive bezel, and a processing element. The housing may include a bottom wall, one or more side walls and a bezel enclosing an internal cavity of the housing. The bezel may at least partially surround a display. The electrically-conductive plate may be coupled to the bottom wall and configured to physically contact the skin on a wearer's wrist when the electronic fitness device is worn. The one or more side walls or the bezel may include an electrically-conductive contact point configured to receive physical contact from the skin of the wearer's finger or thumb. The processing element may be electrically coupled with the plate and the electrically-conductive contact point, the processing element configured to generate an electrocardiogram waveform associated with the user based on electrocardiogram signals received through the electrically-conductive plate and the electrically-conductive surface once physical contact is made between the wearer's wrist and the electrically-conductive plate and between the electrically-conductive contact point and the wearer's finger or thumb. The processing element may be further configured to generate, and store in a memory element, electrocardiogram data based on the electrocardiogram waveform and generate an electrocardiogram image based on the stored electrocardiogram data. The processing element may control the display to present the electrocardiogram image.

Various implementations of the embodiment may include any one or more of the following features. The processing element may be further configured to generate a sequence of electrocardiogram images, wherein each electrocardiogram image may correspond to one sequence of heartbeats of the wearer for a period of time. The processing element may be further configured to generate a stream of electrocardiogram images, wherein the stream of electrocardiogram images may correspond to a plurality of heartbeats of the wearer. The processing element may scroll the electrocardiogram images on the display such that a most-recently generated electrocardiogram image is continuously presented on the display.

In embodiments, the electronic device may further comprise a location determining element configured to determine a geolocation based on location determining signals received by an antenna and a portion of the bezel forms the antenna. The processing element may be configured to utilize electrocardiogram signals received through the bezel once physical contact is made with the bezel to generate the electrocardiogram waveform. The location determining component may be configured to utilize location determining signals received by the bezel when physical contact from the wearer's finger or thumb is not made with the bezel.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present technology will be apparent from the following detailed description of the embodiments and the accompanying drawing figures.

BRIEF DESCRIPTION OF THE DRAWING FIGURES

Embodiments of the present technology are described in detail below with reference to the attached drawing figures, wherein:

FIG. 1 is a fragmentary perspective view of an embodiment of an electronic device configured to generate and graphically display an electrocardiogram image corresponding to electrical activity of a wearer's heart, as well as perform one or more additional general and/or fitness-related functions, examples of which are shown, wherein the electronic device is shown adapted to be worn on the wearer's wrist;

Figure 1:
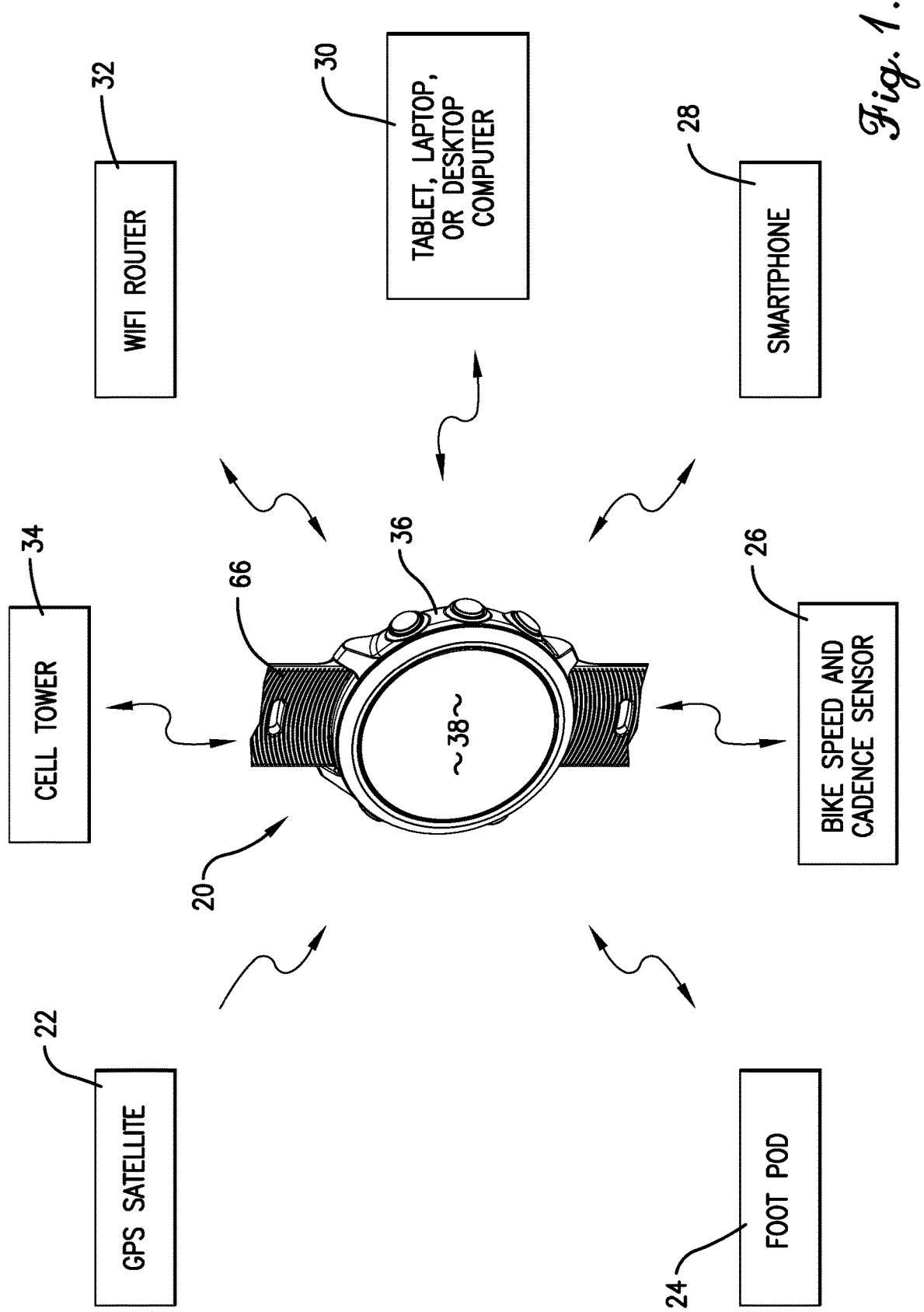

The drawing figures do not limit the present technology to the specific embodiments disclosed and described herein. The drawings are not necessarily to scale, emphasis instead being placed upon clearly illustrating the principles of the technology.

DETAILED DESCRIPTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the present technology. The following detailed description is, therefore, not to be taken in a limiting sense. The scope of the present technology is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Embodiments of the present technology provide an electronic fitness device configured to generate and graphically display an electrocardiogram (ECG) waveform of an electrical activity of a wearer's heart. The electronic device may utilize two contact points to receive electrical bio signals (electrocardiogram signals) from the wearer, from which the electrocardiogram waveform is generated. One contact point may be located on an underside of the electronic device where it may be in generally constant contact with the skin of the wearer's wrist. The other contact point may be a bezel or a portion of the bezel that may also function as an antenna, or a pushbutton that may also depress or rotate to provide a user input interface enabling access of additional functionality.

The electronic fitness device 20 may take substantially any suitable form, such as a wrist-worn fitness watch as shown in FIG. 1, a wrist- or arm-worn smartphone, a wrist- or arm-worn navigation device, or other wearable multi-function electronic devices that include a housing and a band, strap, or other attachment mechanism to secure the electronic fitness device 20 to a user's wrist, arm, ankle or leg. Although the electronic fitness device 20 is described herein as being adapted to be worn on a wrist, it may additionally or alternatively be adapted to be worn on other parts of the body, such as the user's forearm or the upper arm. The wearer of the electronic fitness device 20 may be involved in various physical activities such as street running, trail running, jogging, hiking, walking, biking, swimming, exercising, etc. During these activities, in addition to monitoring the electrical activity of the wearer's heart, the electronic fitness device 20 may determine and monitor a current location of the electronic fitness device 20 by receiving wireless location signals from a satellite-based positioning system 22 such as GPS. The electronic fitness device 20 may utilize the determined location to determine and monitor a distance traveled, a velocity, and other performance metrics. In addition, the electronic fitness device 20 may be electronically paired with one or more other electronic devices, such as a foot pod 24 attached to the user's shoe for measuring jogging or running cadence and distance traveled, or a bike speed and cadence sensor 26 attached to a crank arm and wheel hub of the user's bicycle for tracking biking performance, and so forth. Furthermore, the electronic fitness device 20 may be able to communicate with smartphones 28, tablets, laptop or desktop computers 30, Wi-Fi routers 32, cell towers 34, and the like to allow the user to upload activity data, download apps, receive text messages, emails, and weather alerts, and so on.

Broadly characterized, embodiments of the electronic fitness device 20 may include first and second contact points, a processing element, and a display. The first contact point may be located on an underside (a bottom surface) of the electronic fitness device 20 where it may be in constant contact with the skin of a wearer's wrist when worn by a user. The second contact point may be an electrically-conductive bezel (or a portion of the bezel) that functions as one or more antennas for of the device. For instance, the bezel may provide at least a portion of an antenna coupled with a location determining element. The bezel or portion thereof may be accessible to receive a touch from a user's finger or thumb (of the opposite hand) to initiate the sensing and monitoring of the electrical activity of the wearer's heart. In particular, the electronic fitness device 20 may be configured to perform the location determining function and the heart monitoring function simultaneously or it may be configured to switch between the these functions, in which case the function of the bezel may be selected by system processing element 64 to correspond to a desired function.

Additionally or alternatively, the second contact point may be a pushbutton that is accessible to receive a touch from a user's finger or thumb (of the opposite hand) to initiate the sensing and monitoring of the electrical activity of the wearer's heart. The pushbutton may also be depressed or rotated to access and/or initiate additional general, fitness, or non-fitness-related functionality of the electronic fitness device 20.

The processing element may be a general or dedicated processing element configured to receive a first electrical bio signal (electrocardiogram signal) from the first contact point and a second electrical bio signal (electrocardiogram signal) from the second contact point. The second contact point may be an electrically-conductive bezel or an electrically-conductive pushbutton that is electrically coupled with the processing element. The processing element may be configured to determine the electrical activity of the wearer's heart based on electrical bio signals received through the first contact point and the second contact point once physical contact is made between the wearer's wrist and the first contact point and between the second contact point and the wearer's finger or thumb. The processing element may generate, and store in a memory element, electrocardiogram data based on the electrocardiogram waveform and generate an electrocardiogram image based on the stored electrocardiogram data. The processing element may be further configured to control the display to present determined electrical activity as an electrocardiogram waveform image, a sequence of single waveform images, or a stream of multiple waveform images.

Figure 2:
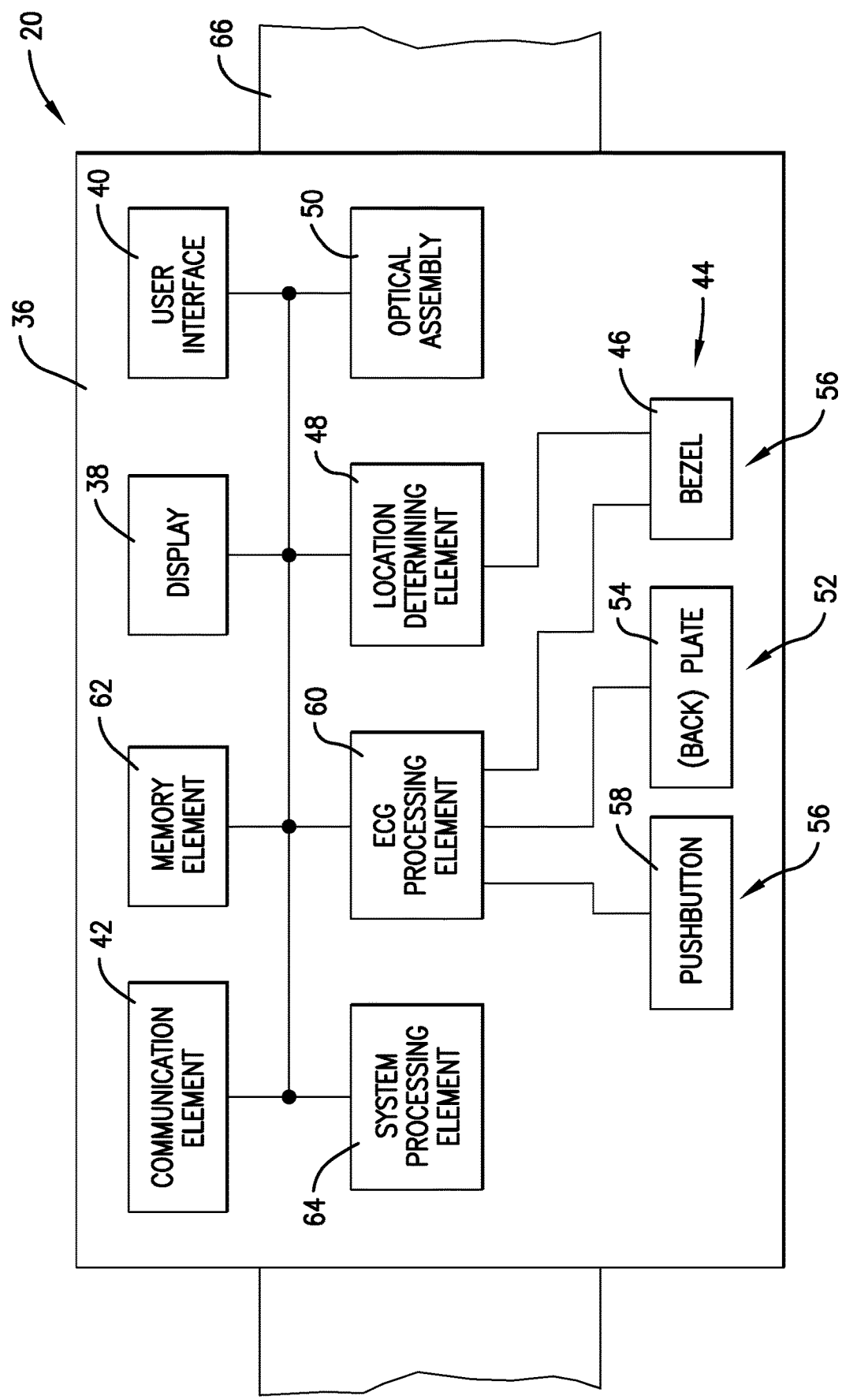
FIG. 2 is a block diagram of at least a portion of functional components of the electronic device of FIG. 1.

Embodiments of the technology will now be described in more detail with reference to the drawing figures. Referring to FIG. 2, an embodiment of the electronic fitness device 20 is shown broadly comprising a housing 36, a display 38, a user interface 40, a communication element 42, one or more antennas 44 (one of which may be a bezel 46), a location determining element 48, an optical assembly 50, a first contact point 56 in the form of the bezel 46 and/or a pushbutton 58, a second contact point 52 in the form of a back plate 54, a memory element 62, and a system processing element 64.

The memory element 62 may include electronic hardware data storage components such as read-only memory (ROM), programmable ROM, erasable programmable ROM, random-access memory (RAM) such as static RAM (SRAM) or dynamic RAM (DRAM), cache memory, or the like, or combinations thereof. In some embodiments, the memory element 62 may be embedded in, or packaged in the same package as, the system processing element 64. The memory element 62 may include, or may constitute, a "computer-readable medium". The memory element 62 may store the instructions, code, code statements, code segments, software, firmware, programs, applications, apps, services, daemons, or the like that are executed by the system processing element 64. The memory element 62 may also store settings, data, documents, sound files, photographs, movies, images, databases, and the like.

The system processing element 64 may include electronic hardware components such as processors, microprocessors (single-core or multi-core), microcontrollers, DSPs, FPGAs, analog and/or digital application-specific integrated circuits (ASICs), or the like, or combinations thereof. The system processing element 64 may generally execute, process, or run instructions, code, code segments, code statements, software, firmware, programs, applications, apps, processes, services, daemons, or the like. The system processing element 64 may also include hardware components such as finite-state machines, sequential and combinational logic, and other electronic circuits that can perform the functions necessary for the operation of the current invention. The system processing element 64 may be in communication with the other electronic components through serial or parallel links that include universal busses, address busses, data busses, control lines, and the like.

It is to be understood that, in some embodiments, the system processing element 64 may include an electrocardiogram (ECG) processing element 60 and perform all of the associated functions described herein. Similarly, in some embodiments, the system processing element 64 may include a heart rate monitor (HRM) processing element 88 and perform all of the associated functions described herein. In other embodiments, the system processing element 64 may be communicatively coupled with the ECG processing element 60 and the HRM processing element 88. In some embodiments, the system processing element 64 may include the location determining element 48 and perform all of the associated functions described herein.

Figure 3:
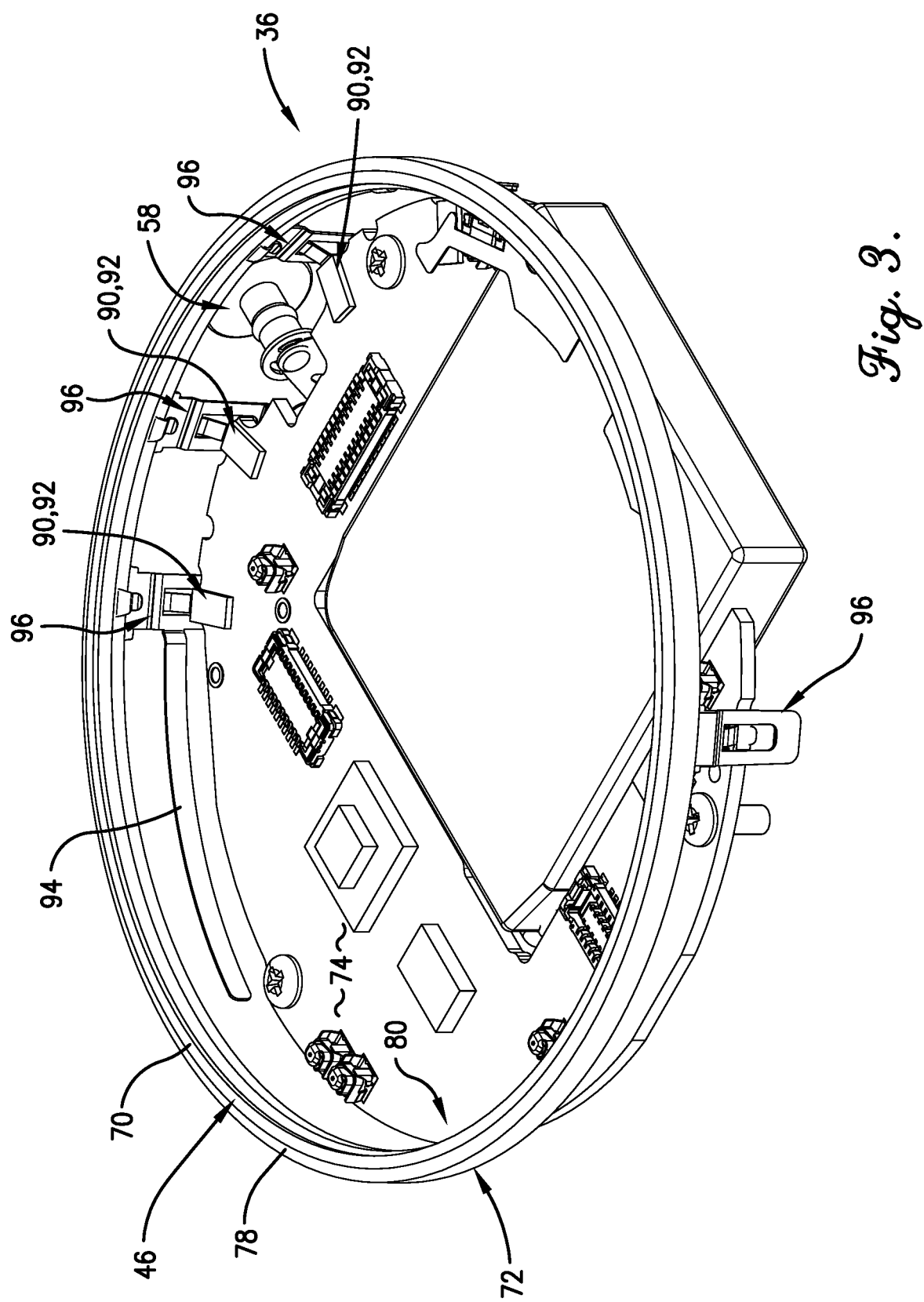
FIG. 3 is an upper isometric view of at least a portion of the functional components retained within a housing of the electronic device of FIG. 1.
Figure 4:
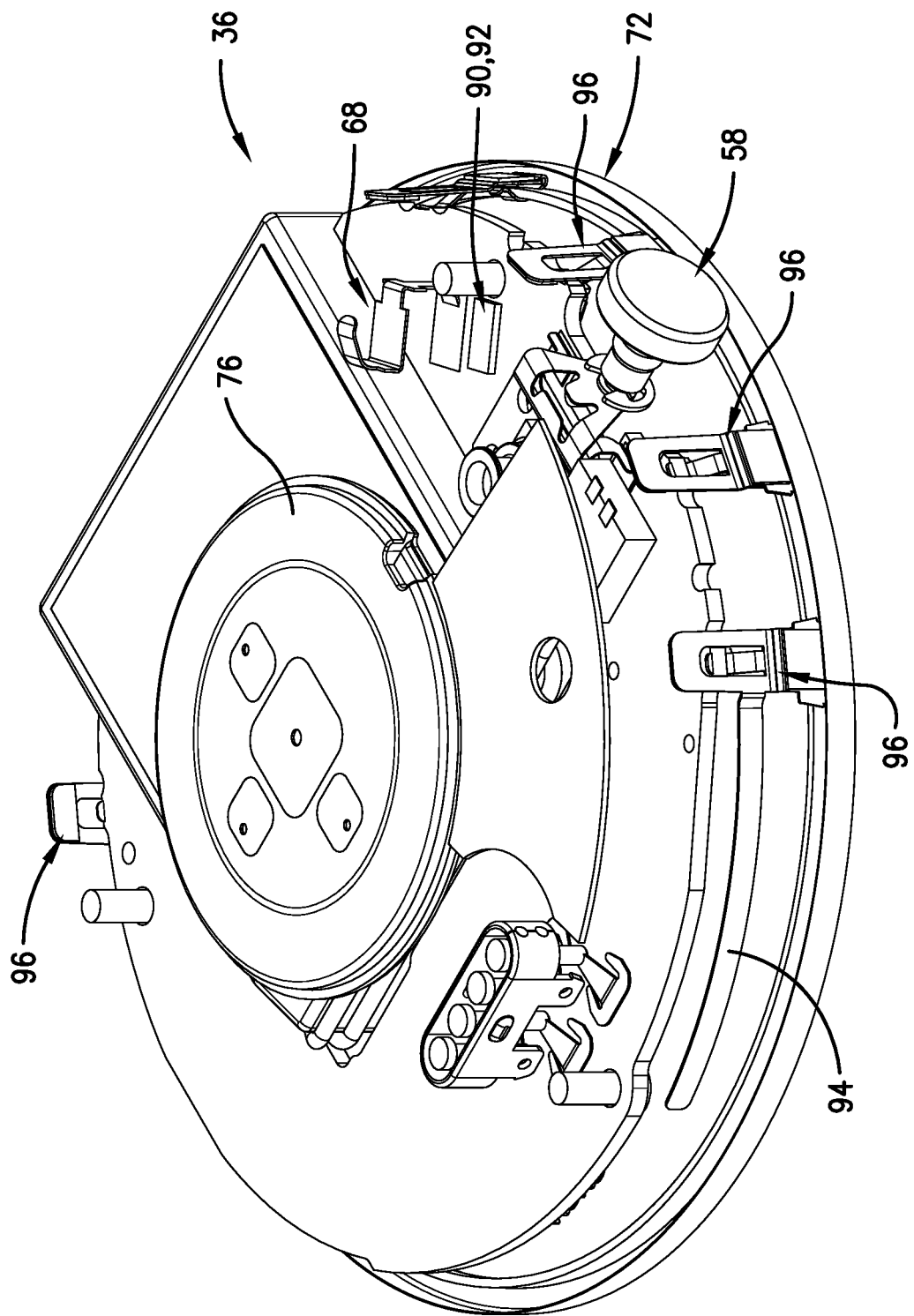
FIG. 4 is a lower isometric view of at least a portion of the functional components retained within the housing of the electronic device of FIG. 1.
Figure 7:
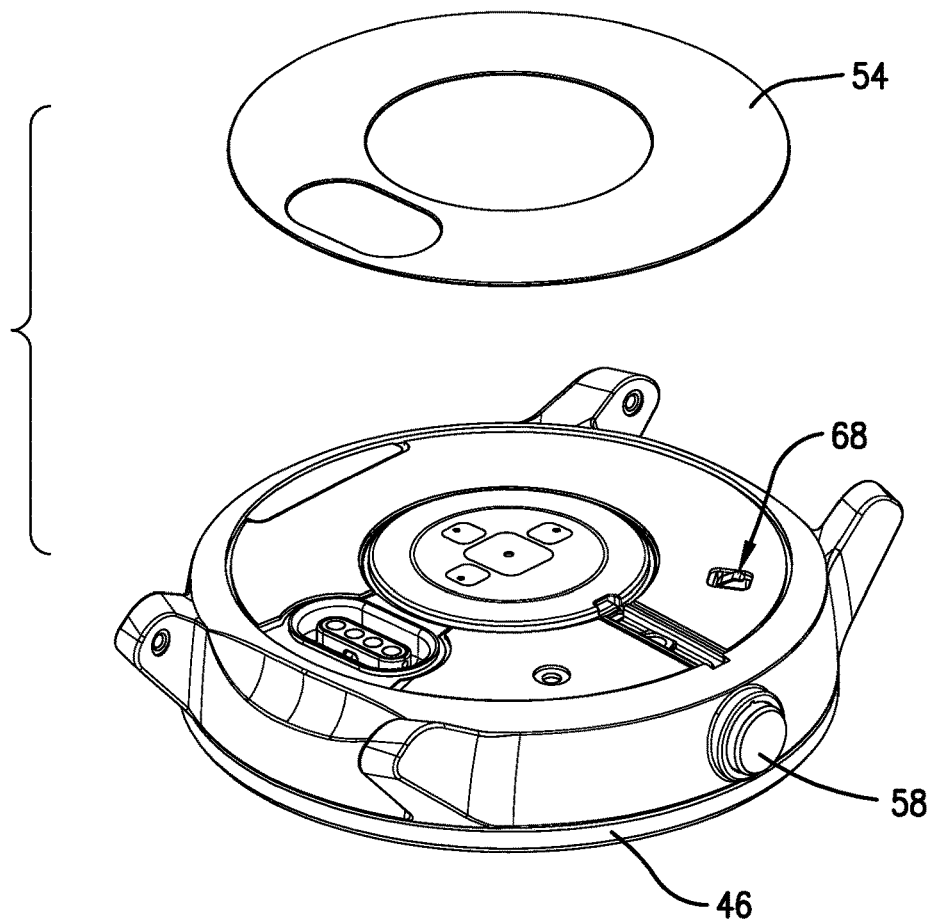
FIG. 7 is a lower view of at least a portion of the housing of the electronic device of FIG. 1.
Figure 8:
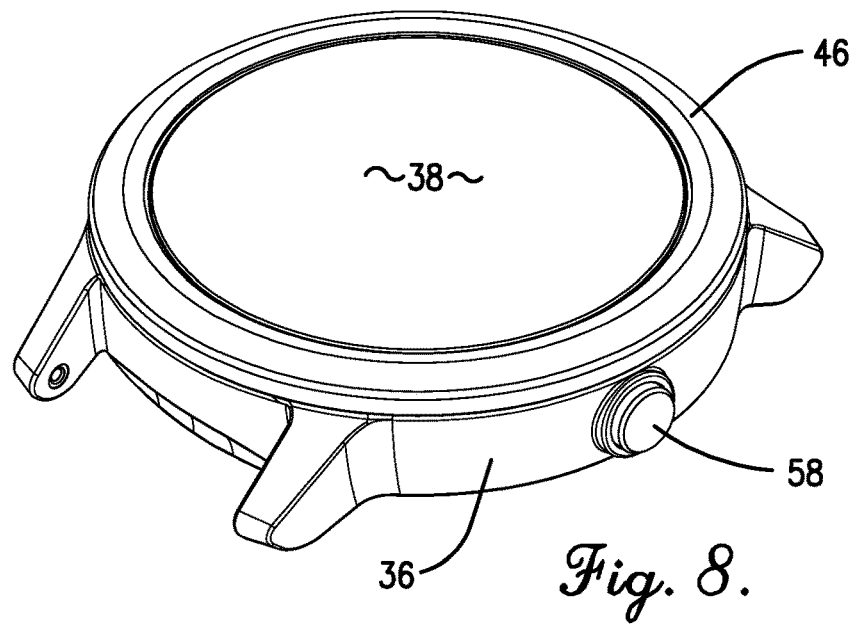
FIG. 8 is an upper view of at least a portion of the housing of the electronic device of FIG. 1.

Referring also to FIGS. 2-4, the housing 36 may generally house, retain, enclose and/or otherwise physical support other components of the electronic fitness device 20 and may include or be coupled to an attachment mechanism 66, such as a wrist or arm band, for securing or retaining the electronic fitness device 20 on or to a body part (limb) of a wearer. The housing 36 may include a lower wall 68, an upper wall 70, at least one side wall 72, and an internal cavity 74. The lower wall 68 may include a lower surface 76 that contacts the wearer's skin, such as the skin on the wearer's wrist or arm, while the user is wearing the electronic fitness device 20. For instance, as shown in FIGS. 7 and 8, lower surface 76 may include the back plate 54. In embodiments, an inner surface (facing internal cavity 74) of back plate 54 may contact a conductive element, such as a surface of a c-shaped spring 68, coupled with ECG processing element 60.

In some embodiments, the lower wall 68 may not be continuous, but may include an opening of circular, square, rectangular, or other geometric shape. The upper wall 70, which may be formed by bezel 46, generally opposes the lower wall 68 and may include an upper surface 78. In some embodiments, the upper surface 78 may further include an opening 80 of circular, square, rectangular, or other geometric shape. The internal cavity 74 may contain and/or retain many of the other components of the electronic fitness device 20. In some embodiments, such as the exemplary embodiments shown in the figures, the lower wall 68 of the housing 36 may have a round, circular, or oval shape with a single circumferential side wall, while in other embodiments, the lower wall 68 may have a four-sided shape, such as a square or rectangle, or other polygonal shape, with the housing 36 including four or more sidewalls. The upper wall 70 may generally match the shape of the lower wall 68.

In embodiments, the c-shaped spring 68 is formed of an electrically-conductive material, such as a metal, to electronically couple back plate 54 of the lower surface 76 to ECG processing element 60. The c-shaped spring 68 may sufficiently flex when under force to enable a secure contact point with the inner surface (facing internal cavity 74) of back plate 54.

The display 38 may generally show or present information, such as time of day, current location, and the like, as well as cardiovascular information, such as heart rate, breathing rate, cardiac parameters, or electrocardiogram (ECG) images. The ECG images presented on display 38 may include the information shown in FIGS. 9 and 10. The display 38 may be implemented using substantially any suitable technology, such as light-emitting diode (LED), organic LED (OLED), Light Emitting Polymer (LEP) or Polymer LED (PLED), liquid crystal display (LCD), thin film transistor (TFT) LCD, LED side-lit or back-lit LCD, or the like, or combinations thereof. In some embodiments, the display 38 may have a round, circular, or oval shape. In other embodiments, the display 38 may have a square or a rectangular aspect ratio which may be viewed in either a landscape or a portrait orientation. The display 38 may be at least partially positioned in the internal cavity 74 of the housing 36, such that the display 38 is adjacent to the opening 80 of the upper surface 78 of upper wall 70, which may be formed by bezel 46. The electronic fitness device 20 may further include a lens or other covering (not shown) positioned on an upper surface of the display 38 to enhance the visibility of the information presented on the display 38.

The user interface 40 may generally allow the user to directly interact with the electronic fitness device 20 and may include the pushbutton 58, as well as other buttons, knobs, switches, or the like, and combinations thereof. Additionally or alternatively, the display 38 may include a touch screen occupying the entire display 38 or a portion thereof or be otherwise configured so that the display 38 functions as at least a portion of the user interface 40. The touch screen may allow the user to interact with the electronic fitness device 20 by physically touching, swiping, or gesturing on areas of the display 38 to input information or configure the electronic fitness device 20.

The communication element 42 may generally allow communication with external systems or devices. The communication element 42 may include signal or data transmitting and receiving circuits, such as amplifiers, filters, mixers, oscillators, digital signal processors (DSPs), and the like. Various combinations of these circuits may form a transceiver, which transmits, receives, and processes signals such as those listed in the following discussion. The communication element 42 may establish communication wireles sly by utilizing radio frequency (RF) signals and/or data that comply with communication standards such as cellular 2G, 3G, 4G, LTE, or 5G, Institute of Electrical and Electronics Engineers (IEEE) 802.11 standard such as Wi-Fi, IEEE 802.16 standard such as WiMAX, Bluetooth™, or combinations thereof. In addition, the communication element 42 may utilize communication standards such as ANT, ANT+, Bluetooth™ low energy (BLE), the industrial, scientific, and medical (ISM) band at 2.4 gigahertz (GHz), or the like. The communication element 42 may be in electronic communication with the memory element 62 and the system processing element 64. In various embodiments, the electronic fitness device 20 may be configured to establish communication with more than one protocol or standard, and the communication element 42 may include a transceiver for each protocol or standard, such as Bluetooth™, Wi-Fi, cellular, etc., with which the electronic fitness device 20 can communicate. In addition, the communication element 42 may further include or be electrically coupled with the one or more antennas 44, which allow the electronic fitness device 20 to transmit and receive wireless signals to and from exercise-related sensors, such as the foot pod 24, the bike speed and cadence sensor 26, or the like, other electronic devices, such as the smartphone 28, the tablet, the laptop, or the desktop computer 30, or communication network interfaces such as the Wi-Fi router 32 or the cell tower 34.

The location determining element 48 may generally determine a current geolocation of the electronic fitness device 20 by receiving and processing radio frequency (RF) electronic signals from a global navigation satellite system (GNSS) such as the global positioning system (GPS) primarily used in the United States, the GLONASS system primarily used in the Soviet Union, or the Galileo system primarily used in Europe. The location determining element 48 may include satellite navigation receivers, processors, controllers, other computing devices, or combinations thereof, and memory. The location determining element 48 may further include or be electrically coupled with the antenna 44, from which it may receive a location wireless signal from one or more of the previously-mentioned satellite systems and may generate an electrical geolocation signal. As discussed above, antenna 44 may include a portion of bezel 46, which may be an electrically-conductive watch bezel. The location determining element 48 may process data included in the location electronic signals received by antenna 44 from which geographic information such as the current geolocation is determined. The current geolocation may include geographic coordinates, such as the latitude and longitude, of the current location of antenna 44 and the electronic fitness device 20. The location determining element 48 may communicate the current geolocation to the system processing element 64.

Although embodiments of the location determining element 48 may include a satellite navigation receiver, it will be appreciated that other location-determining technology may be used. For example, cellular towers or any customized transmitting radio frequency towers can be used instead of satellites may be used to determine the location of the electronic fitness device 20 by receiving data from at least three transmitting locations and then performing basic triangulation calculations to determine the relative position of the device with respect to the transmitting locations. With such a configuration, any standard geometric triangulation algorithm can be used to determine the location of the electronic fitness device 20. The location determining element 48 may also include or be coupled with a pedometer, accelerometer, compass, or other dead-reckoning components which allow it to determine the location of the electronic fitness device 20. The location determining element 48 may determine the current geographic location through a communications network, such as by using Assisted GPS (A-GPS), or from another electronic device. The location determining element 48 may even receive location data directly from a user.

As shown in FIGS. 3 and 4, a plurality of latch connectors 96 may electrically couple the bezel 46 with location determining element 48 and an ECG processing element 60, which may be integrated within the system processing element 64 or separate from the system processing element 64. Each latch connector 96 may pass location signals from bezel 46 to the location determining element 48 and bio signals (electrocardiogram signals) from bezel 46 to the ECG processing element 60. The latch connectors 96 are typically located within the inner cavity 74 of the housing 36. In embodiments, any of the latch connector 96 may be coupled with a switch 90, 92 to isolate (open circuit) or pass (closed circuit) electrical signals, such as the location signals and the bio signals (electrocardiogram signals).

As shown in FIGS. 3 and 4, in embodiments, each signal terminal coupled with bezel 46 and the c-shaped spring 68 coupled with back plate 54 may have a switch 90, 92 located between the respective signal terminal or c-shaped spring 68 and the system processing element 64 or ECG processing element 60. Each of the switches 90, 92 may be controlled by the system processing element 64 to cause isolation (open circuit) or conductivity (closed circuit) of the associated component (bezel 46 or c-shaped spring 68). For instance, the signal terminals of bezel 46 may include signal feed (F) and electrical ground (G) terminals that may be isolated or conducted through based on a selected position of an associated switch 90, 92.

In embodiments, the system processing element 64 may select an operating mode by interacting with switches 90, 92 to couple bezel 46 with the location determining element 48 or the ECG processing element 60. For example, the system processing element 64 may output control signals to close a first switch 90 and opening a second switch 92 to put the electronic fitness device 20 to select a GPS mode. Similarly, the system processing element 64 may output control signals to open the first switch 90 and close the second switch 92 to select an ECG mode.

Figure 5:
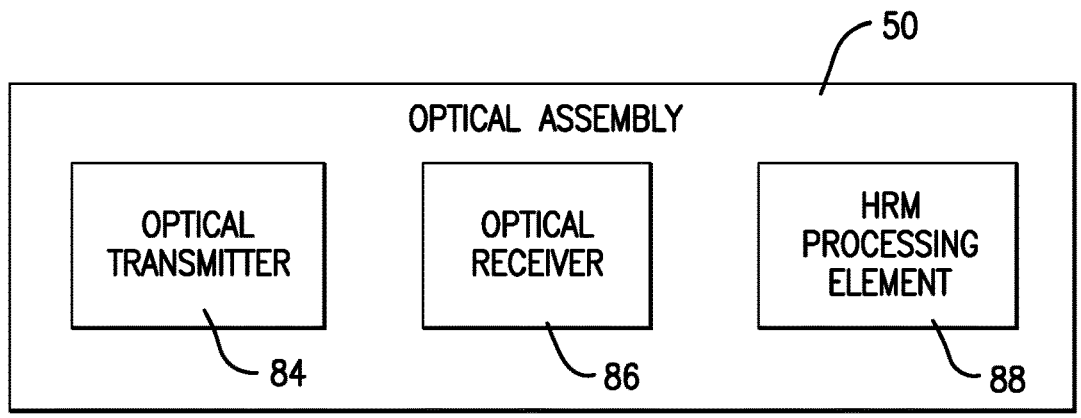
FIG. 5 is a block diagram of a heart rate monitoring assembly of the electronic device of FIG. 1.

Referring also to FIG. 5, the optical assembly 50 may generally measure the blood flow in an area proximity to the optical assembly 50. For instance, optical assembly 50 may output light and identify changes in the volume of blood in the wearer's capillaries based on reflections of the outputted light from the area. The optical assembly 50 may generate a plethysmogram (PPG) signal based on the intensity of the reflected light and system processing element 64 may determine one or more cardiac performance metrics, such as heart rate, based on the PPG signal.

For example, the optical assembly 50 may use optoelectronic technology including an optical transmitter 84 (e.g., an LED or similar photo transmitters), an optical receiver 86 (e.g., a photodiode, a photodetector or similar photo receivers), and an HRM processing element 88. The optical transmitter 84 illuminates the wearer's skin and some of the transmitted light is reflected and received by the optical receiver 86, which outputs a PPG signal having a magnitude corresponding to the intensity of the reflected light received by the optical receiver 86. The HRM processing element 88 may include digital signal processors (DSPs), field-programmable gate arrays (FPGAs), or the like and may utilize the PPG signal to determine a heart rate or pulse (estimated heart beats per minute (bpm)) for the user. The determined cardiac performance metric, such as heart rate or pulse, may be communicated to the memory element 62 and the system processing element 64, such as in the form of an electrical HRM signal.

The bezel 46, which in one embodiment may form the first contact point 56, may be formed from an electrically-conductive material. The bezel 46 may have substantially any suitable shape, such as a shape that generally corresponds to the shape of the housing 36 or a portion thereof, and may be located on a periphery of the upper wall 70 or the side wall 72 of the housing 36. Bezel 46 may at least partially surround display 38. The bezel 46 may form a portion of antenna 44 coupled with location determining element 48.

In embodiments, different portions of bezel 46 may form a plurality of antennas 44. For example, portions of bezel 46 may form a portion of a first antenna, a second antenna, and a third antenna. The first antenna may be configured to receive a first wireless signal, such as a GPS signal, and generate a corresponding first electronic signal that is provided to the location determining element 48. The first antenna may be of a slot-antenna type and may be formed from a first electronic signal terminal, a first and a second electrical ground terminals, and a first portion of a circumference of the bezel 46. The second antenna may be configured to transmit and receive a second wireless signal, such as Bluetooth, Wi-Fi, cellular, etc., and may transmit and receive a corresponding second electronic signal. The second antenna may also be of the slot-antenna type and may be formed from a second electronic signal terminal, third and fourth electrical ground terminals, and a second portion of the circumference of the bezel 46. The third antenna may be configured to transmit and receive a third wireless signal, such as Bluetooth, Wi-Fi, cellular, etc., and may transmit and receive a corresponding third electronic signal. In embodiments, as shown in FIGS. 3-4, the third antenna 94 may be of an inverted F-antenna type and may be formed from a third electronic signal terminal, a first latch connector 96, an antenna strip electrically connected to the first latch connector 96, a fifth electrical ground terminal, and a third portion of the circumference of the bezel 46. Each of the antennas within antenna 44 may transmit and/or receive signals at a different frequency. By utilizing an electrically-conductive bezel 46 that forms a portion of three separate antennas, the electronic fitness device 20 is able to simultaneously receive GPS signals and wirelessly communicate with at least two other devices or networks.

The back plate 54 which forms the second contact point 52 may be formed from an electrically conductive material, may have substantially any suitable shape, and may be located on the lower surface 76 of the lower wall 68 of the housing 36, so that it is generally in constant contact with the wearer's skin. The back plate 54 may be configured to receive a first electrical bio signal (electrocardiogram signal) via the wearer's skin, and to provide the first electrical bio signal to the ECG processing element 60.

Figure 6A:
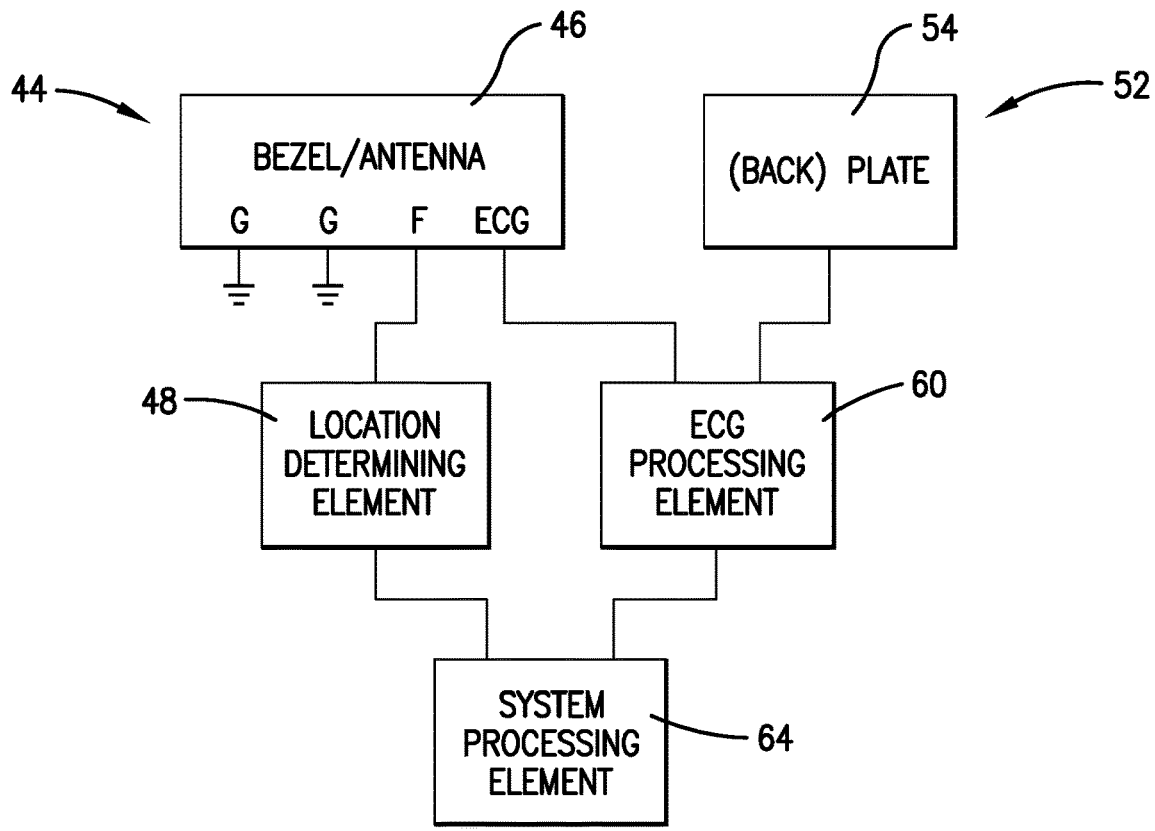
FIG. 6A is a block diagram of a first implementation of an embodiment of an electrocardiogram subsystem for monitoring an electrical activity of a heart of a wearer of the electronic device of FIG. 1.
Figure 6B:
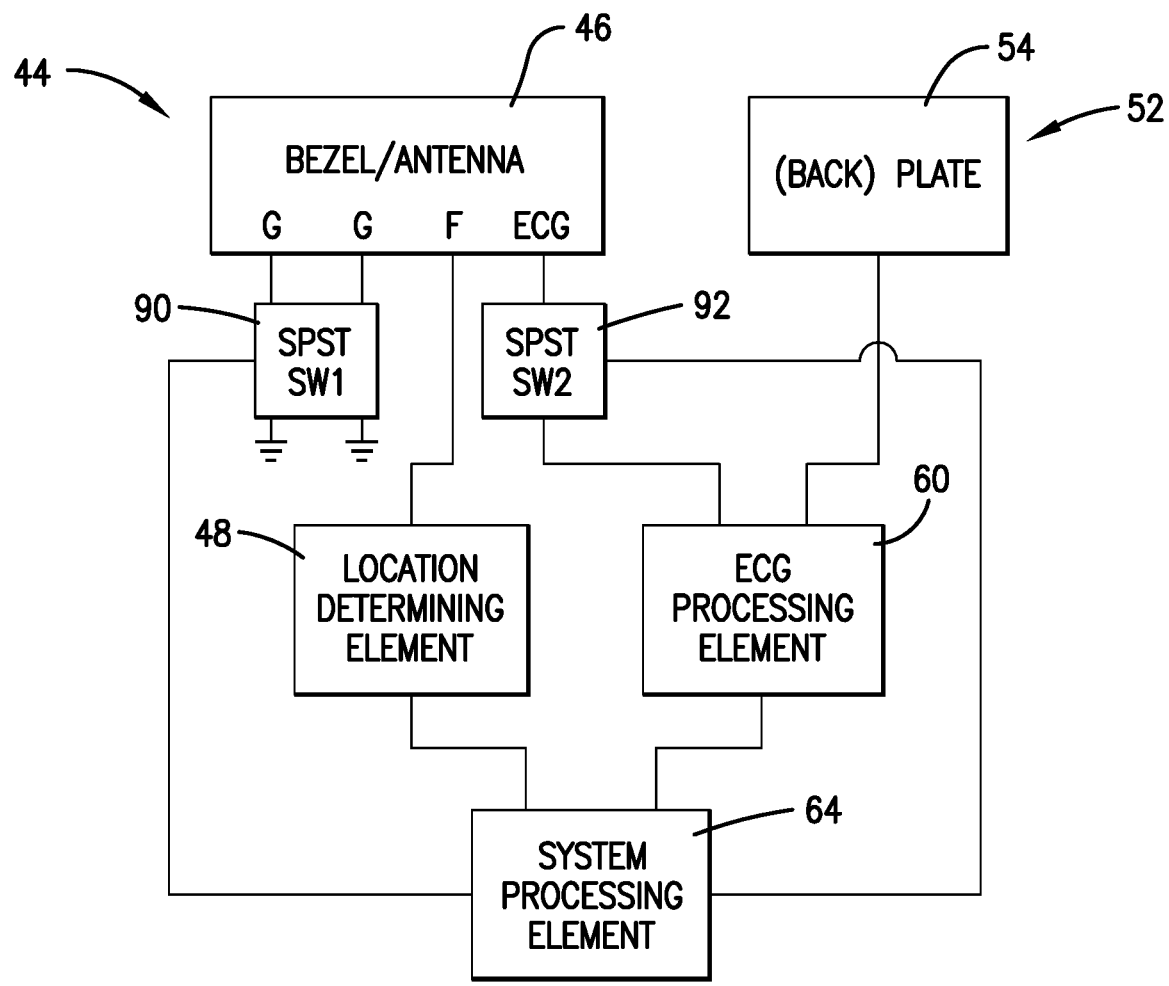
FIG. 6B is a block diagram of a second implementation of the embodiment of the electrocardiogram subsystem.

As seen in FIGS. 6A and 6B, the bezel 46 may include electrical ground terminals, indicated by the letter "G", a signal feed terminal, indicated by the letter "F," and an ECG signal terminal, indicated by the letters "ECG." When processing system 64 determines to use bezel 46 as antenna 44, which utilizes the electrical ground (G) and signal feed (F) terminals for operation as described above, the received signals are provided to the location determining element 48 from the signal feed (F) terminal.

In embodiments, the system processing element 64 may control one or more switches 90, 92 to cause isolation (open circuit) of bezel 46 from the ECG signal (ECG) terminal when the bezel 46 is desired to be used to receive location signals from GPS satellites or communication signals from remote devices and conductivity (closed circuit) of bezel 46 with the signal feed (F) and electrical ground (G) terminals.

When bezel 64 is used as a first contact point 56, the first electrical bio signals (electrocardiogram signals) received from the first contact point 56 are provided to the ECG processing element 60, which may be a part of the system processing system 64. In embodiments, when processing system 64 determines to use bezel 46 to serve as a first contact point 56 to receive the first electrical bio signals, the system processing element 64 may control the one or more switches 90, 92 to cause isolation of bezel 46 from the signal feed (F) and one or more ground (G) terminals and conductivity (closed circuit) of bezel 46 with the ECG signal (ECG) terminal.

As shown in FIG. 6B, a switch 90 may be used to isolate (open circuit) or pass (closed circuit) location signals from bezel 46 to location determining element 48. In such embodiments, switch 90 may be opened for two ground (G) terminals reduce the location signals passed to the location determining element 48 from bezel 46 and closed to increase location signals passed to the location determining element 48 from bezel 46. A switch may not be positioned between the signal feed (F) terminal of bezel 46 and the location determining element 48 because some (reduced) location signals may continue to pass to the location determining element 48.

In embodiments, the first electrical bio signals may be received from the wearer and communicated to the ECG processing element 60 at any time, and as long as, the wearer physically contacts the bezel 46 with a finger or thumb of his other hand. In other embodiments, the system processing element 64 controls display 38 to notify the user that the bezel 46 may be contacted with a finger or thumb of his other hand once the switches 90, 92, which were previously isolating bezel 46 from the ECG signal (ECG) terminal when the bezel 46 is desired to be used to receive location signals from GPS satellites or communication signals from remote devices, are closed to enable bezel 64 to act as a first contact point 56 by passing first electrical bio signals (electrocardiogram signals) to ECG processing element 60.

With reference to FIG. 6B, the electronic fitness device 20 may include a first single-pole, single-throw (SPST) switch 90 and a second SPST switch 92. The switches 90, 92 may make or break electrical contact between two connection points of a signal. As seen in FIG. 6B, the first switch 90 may make electrical contact (switch closed) or break electrical contact (switch open) with one or more electrical ground points of the bezel 46. The second switch 92 may make or break electrical contact second electrical bio signal from the ECG contact of the bezel 46. Each switch 90, 92 may further include a control line, which controls whether the switch makes or breaks electrical contact. As detailed herein, the system processing element 64 may send a signal to each control line to open or close the first switch 90 and the second switch 92.

In embodiments, the system processing element 64 may default to closing the first switch 90 and opening the second switch 92 to put the electronic fitness device 20 in GPS mode. If the system processing element 64 determines that the location signals received by location determining element 48 are attenuated (e.g., as a result of the wearer contacting the bezel 46 or a loss of GPS signal), or if the wearer provides an input using user interface 40 to select the ECG mode, the system processing element 64 may send signals to open the first switch 90 and close the second switch 92. The closing of the second switch 92 allows the ECG processing element 60 to receive the electrical bio signal, and in turn, generate an ECG waveform that is used to generate an electrocardiogram image. When the wearer removes physical contact of his finger or thumb from the bezel 46 (or provides an input provides an input using user interface 40 to select the GPS mode), the system processing element 64 may close the first switch 90 and open the second switch 92.

The pushbutton 58 may be part of the user interface 40 and may include a spring-loaded button that is coupled to a normally-closed (NC) or normally-open (NO) electrical contact. The pushbutton 58 may be constructed from an electrically-conductive material and may have substantially any suitable shape. The pushbutton 58 may have a shaft that passes through an opening located on the side wall 72 of housing 36. The contact of pushbutton 58 may be positioned between two spaced apart electrodes and may make or break electrical connection with the two electrodes depending on the position of pushbutton 58—pushed or not pushed—as is generally known for pushbutton operation. Additionally, pushbutton 58 may be rotated to provide user input.

In embodiments, the pushbutton 58 may form the first contact point 56 for generating ECG signals. As a result, the pushbutton 58 may include two outputs. A first output may provide the first electrical bio signal (electrocardiogram signals) to ECG processing element 60. A second output may be provided by the electrical contact and may include a user interface signal. The system processing element 64 may select use of the second output when the first electrical bio signal is desired to be communicated to the ECG processing element 60 and may be based on a determination by the system processing element 64 that the wearer is physically contacting pushbutton 58 with his skin, such as by using a finger or thumb of the opposing hand. The user interface signal may be communicated to the system processing element 64 and may be generated when the wearer presses (or presses and releases) the pushbutton 58 or rotates the pushbutton 58. The user interface signal may be a pulse or a steady state signal.

The ECG processing element 60 may be configured to receive the first and second electrical bio signals (electrocardiogram signals) from the first and second contact points 56, 52, and determine or detect the electrical activity of the wearer's heart. The first and second electrical bio signals (electrocardiogram signals) represent action potentials that cause muscle contraction due to electrical stimulation of the wearer's heart. Typically, two points, the first contact point 56 and the second contact point 52, are used for the detection of the ECG signal. As discussed above, each contact point is typically located on each side of the heart (i.e., the midline the wearer's body). The electronic fitness device 20 worn on the user's left hand may be configured for receiving the first ECG signal from the first contact point 56 on the wearer's right side (from the opposing hand), and the second ECG signal from the second contact point 52 on the wearer's left side (corresponding the wrist on which the electronic fitness device 20 is worn). In embodiments, the ECG processing element 60 or the system processing element 64 may reverse the polarity of the received ECG signals to cause the displayed ECG image(s) to be inverted.

In an exemplary embodiment, the ECG processing element 60 may include an instrumentation amplifier, an analog-to-digital converter (ADC), and an optional microprocessor. The ECG processing element 60 may include suitable custom or off-the-shelf chips or other devices. For example, the instrumentation amplifier may be embodied by the AD8233 ECG Heart Rate Monitor integrated circuit (IC), available from Analog Devices, Inc., which is configured or configurable to extract, amplify, and filter small biopotential signals under noisy conditions.

In operation, the instrumentation amplifier of the ECG processing element 60 may receive the second electric signal from the second contact point 52 (the back plate 54) constantly while the user is wearing the electronic fitness device 20. The instrumentation amplifier may wait for the presence of the first electric signal from the first contact point 56. The amplitude of the first and second electrical bio signals (electrocardiogram signals) may be between 0.2 and 5.0 mV. Once the first contact point 56 begins providing the first electrical bio signal, the ECG processing element 60 may control its instrumentation amplifier to amplify the signal (by, for instance, between 800:1 and 1000:1), reduce or remove any noise resulting from amplifying the signal, and generate an analog ECG waveform.

The instrumentation amplifier of the ECG processing element 60 may also provide a "leads off" detection function, where a leads off signal is generated to indicate that the first and second electrical bio signals from the wearer have been detected. The ECG processing element 60 may digitize the analog ECG waveform by using an analog-to-digital converter (ADC). The digital ECG waveform may optionally be bandpass filtered. For the embodiments in which system processing element 64 does not include the ECG processing element 60, the ECG waveform may be communicated to the system processing element 64.

By utilizing hardware, software, firmware, or combinations thereof, the processing element 64 may perform the following functions. The system processing element 64 may receive electrical signals from, at the least, the bezel 46, the pushbutton 58, the location determining element 48, the HRM assembly 50, and the ECG processing element 60. The system processing element 64 may control a mode of operation of the electronic fitness device 20 based on whether bezel 46 is to be used to receive location information or cardiovascular (electrocardiogram) information.

The system processing element 64 may control the one or more switches display 38 to present applicable information presented based on the selected mode. For instance, the system processing element 64 may control the one or more switches to cause isolation of bezel 46 from the signal feed (F) and one or more ground (G) terminals and conductivity (closed circuit) of bezel 46 with the ECG signal (ECG) terminal when the processing system 64 determines to use bezel 46 to serve as a first contact point 56 to receive the first electrical bio signals. Similarly, the system processing element 64 may control one or more switches to cause isolation (open circuit) of bezel 46 from the ECG signal (ECG) terminal and conductivity (closed circuit) of bezel 46 with the signal feed (F) and electrical ground (G) terminals when the bezel 46 is desired to be used to receive location signals from GPS satellites or communication signals from remote devices.

In some instances, a current mode of operation may be selected or controlled manually by the wearer by providing an input using the pushbutton 58, which generates a user interface signal when depressed or rotated. For example, upon receipt of the user interface signal, the system processing element 64 may select an active mode, which may be a GPS mode or an ECG mode, among others (e.g., an HRM mode, a blood pressure mode, etc.).

In other instances, a current mode of operation may be selected or controlled automatically when the system processing element 64 receives one or more electrical signals from the location determining element 48, the HRM assembly 50, and/or the ECG processing element 60. For example, if system processing element 64 determines that a user is physically contacting the first contact point 56, which may occur when the user attempts to provide first and second electrical bio signals (electrocardiogram signals), the system processing element 64 may select the ECG mode and control the one or more switches to cause isolation of bezel 46 from the signal feed (F) and one or more ground (G) terminals and conductivity (closed circuit) of bezel 46 with the ECG signal (ECG) terminal. The system processing element 64 may automatically (after a period of 2-5 seconds) select the GPS mode once it determines that the user is no longer physically contacting the first contact point 56.

In embodiments, the system processing element 64 (and the electronic fitness device 20) may default to the GPS mode, in which the location determining element 48 receives GPS signals from antenna 44 that may be partially formed by bezel 46 and communicates the geolocation to the memory element 62 and system processing element 64. In the GPS mode, the system processing element 64 may determine, and control the display 38 to show, related information such as a current geolocation, a distance traveled for a certain period of time, a velocity of travel, a time of travel, and a route traveled. The user interface 40 may be utilized by the wearer to select the information presented on the display 38 by providing inputs to a touch screen or by pressing (, or pressing and releasing) or rotating the pushbutton 58.

In the ECG mode, the system processing element 64 may generate (or receive from the ECG processing element 60) the electrocardiogram waveform based on electrocardiogram signals received through the first contact point once physical contact is made between the bezel and the wearer's finger or thumb and through the second contact point once physical contact is made between the wearer's wrist and the electrically-conductive plate.

The system processing element 64 may determine generate, and store in the memory element 62, electrocardiogram data based on the electrocardiogram waveform. For instance, the electrocardiogram data may determine a QRS complex, a PR interval, a PR segment, a QT interval, a ST segment, a QR complex, an RS complex, and a QS complex based a determined amplitude of the electrocardiogram waveform at each moment for at least a period of time including one heartbeat. The system processing element 64 may also determine a time between any of this electrocardiogram data (e.g., a time between successive QRS complexes). The electrocardiogram data may include a peak-to-peak period determined by the system processing element 64 based on peaks of the electrocardiogram waveform (e.g., by using the QRS complex). In embodiments, the electrocardiogram data may include heart rate variability (HRV), which is a calculated variability between peak-to-peak periods determined for a plurality of heart beats.

Figure 9:
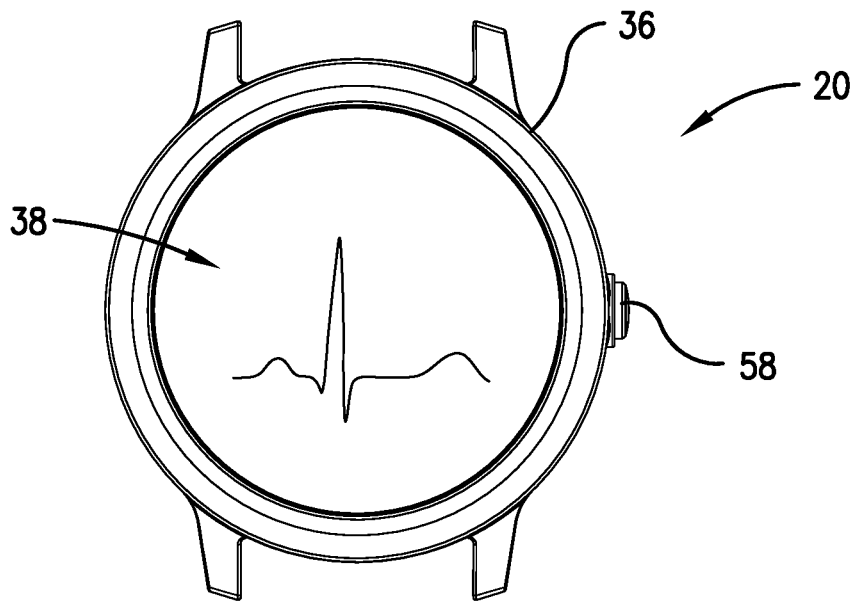
FIG. 9 is a plan view of the electronic device of FIG. 1 displaying a sequence of single electrocardiogram images.
Figure 10:
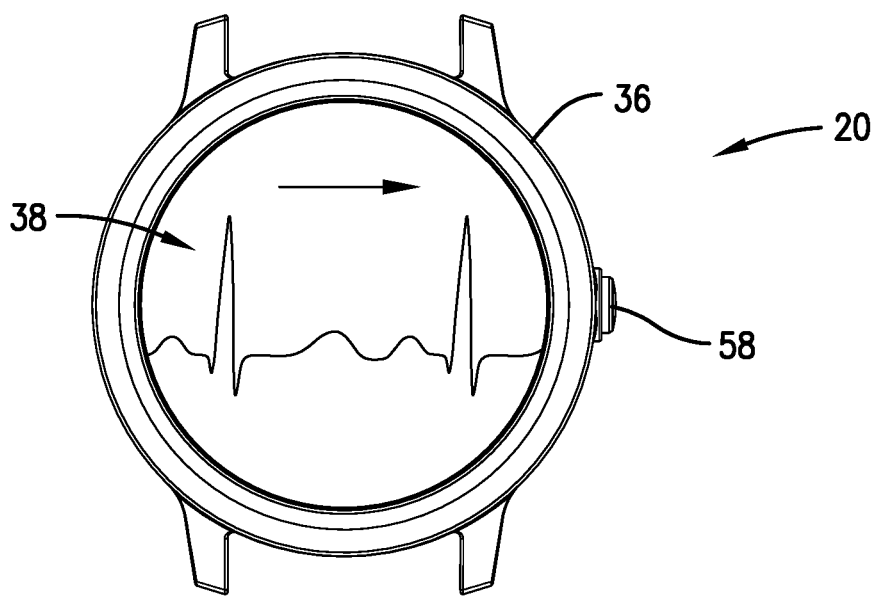
FIG. 10 is a plan view of the electronic device of FIG. 1 displaying a stream of multiple electrocardiogram images.

The system processing element 64 may control the display 38 to present the electrocardiogram waveform as one or more electrocardiogram images. In some embodiments, as shown in FIG. 9, the system processing element 64 may control the display 38 to present a sequence of electrocardiogram images, where each electrocardiogram image corresponds to one sequence of heartbeats of the wearer for a period of time. In other embodiments, as shown in FIG. 8, the system processing element 64 may control the display 38 to present a stream of electrocardiogram images, wherein the stream of electrocardiogram image corresponds to a (a plurality) of heartbeats of the wearer and the electrocardiogram images are scrolled such that a current or most-recently generated electrocardiogram image is continuously presented on the display 38. The direction of streaming may be indicated by an arrow, as shown in FIG. 10.

The user may manually switch between the GPS mode and the ECG mode by pressing (or pressing and releasing) or by rotating the pushbutton 58. Additionally, or alternatively, the system processing element 64 may automatically switch modes depending on, or according to, the electrical signals that determined to be received by bezel 46 and pushbutton 58. For instance, with reference to FIG. 6A, when the system processing element 64 determines that location determining element 48 is receiving location signals (from satellites) and the wearer is not touching the bezel 46 or the pushbutton 58, then the system processing element 64 may control one or more switches to enable use of bezel 46 to receive location signals for use by location determining element 48. Alternatively, if the system processing element 64 determines that the wearer is contacting the bezel 46 (attenuating any location signals received by the bezel 46), then the system processing element 64 may control one or more switches to enable use of bezel 46 to receive an electrical bio signal for use by the ECG processing element 60 to generate the ECG waveform. Alternatively, if the wearer contacts the pushbutton 58, then the ECG processing element 60 may generate the ECG waveform. The location determining element 48 may stop determining a current geographic location without the location signals. In the presence of the ECG signals, the system processing element 64 may automatically switch from the GPS mode to the ECG mode (whether the location signals are present or not). When the system processing element 64 determines that bezel 46 is no longer receiving an ECG signal (as a result of the wearer no longer contacting the bezel 46 and/or the pushbutton 58), the system processing element 64 may select the GPS mode, or the mode that was active prior to the ECG mode.

In the HRM mode, the system processing element 64 may control the display 38 to present cardiac metrics such as values for heart rate (beats per minute), pulse oximetry (VO2 max), breathing rate, and heart rate variability (HRV). The system processing element 64 may determine values of heart rate, VO2 max, breathing rate, heart rate variability (HRV), and the like based on signals received from the optical assembly 50.

In the blood pressure mode, the system processing element 64 may calculate or determine an estimated blood pressure of the wearer. The electrical HRM signal received by the system processing element 64 may include information or data regarding the pressure pulse in the blood resulting from a heartbeat. Unlike an ECG signal (an electrical signal) that travels nearly instantly from the user heart to the contact points of the electronic fitness device 20, the pressure pulse travels more slowly from the heart to the electronic fitness device 20. The system processing element 64 may calculate or determine an approximate distance from the user's heart to electronic fitness device 20 or is entered by the wearer, then the system processing element 64 may calculate a pulse wave velocity as the distance divided by the time taken for the pulse wave to travel to the electronic fitness device 20 worn on the user's wrist. Finally, the system processing element 64 may utilize information stored in memory element 62 to correlate the determined pulse wave velocity to an approximate blood pressure of the wearer. The system processing element 64 may then control the display 38 to present the determined blood pressure value.

Although the technology has been described with reference to the embodiments illustrated in the attached drawing figures, it is noted that equivalents may be employed and substitutions made herein without departing from the scope of the technology as recited in the claims.

Having thus described various embodiments of the technology, what is claimed as new and desired to be protected by Letters Patent includes the following:

1. A wrist-worn electronic device comprising:
   a display;
   a memory element;
   a housing including a bottom wall, one or more side walls, and an electrically-conductive bezel at least partially surrounding the display and positioned to receive physical contact from a wearer's finger or thumb, the bezel at least partially forming an antenna and providing a first contact point;
   a location determining element configured to receive location determining signals from the antenna and configured to determine a geolocation of the electronic device based on the received location determining signals;
   an optical assembly centrally-positioned on the bottom wall, the optical assembly including an optical transmitter configured to output light onto the wearer's wrist and an optical receiver configured to receive light reflected from the wearer's wrist;
   an electrically-conductive plate surrounding the optical assembly, coupled to the bottom wall and configured to physically contact a wearer's wrist when the electronic device is worn, the plate forming a second contact point;
   a plurality of electrical switches; and
   a processing element in electronic communication with the display, the memory element, and the plurality of electrical switches, and electrically coupled with the plate and the bezel, the processing element configured to—
      control the plurality of electrical switches to selectively couple the bezel to the location determining component and the processing element,
      generate an electrocardiogram waveform associated with the wearer based on electrocardiogram signals received through the first contact point once physical contact is made between the bezel and the wearer's finger or thumb and through the second contact point once physical contact is made between the wearer's wrist and the electrically-conductive plate,
      generate, and store in the memory element, electrocardiogram data based on the electrocardiogram waveform,
      generate an electrocardiogram image based on the stored electrocardiogram data, and
      control the display to present the electrocardiogram image.

2. The electronic device of claim 1, wherein the processing element is further configured to generate a sequence of electrocardiogram images, wherein each electrocardiogram image corresponds to one sequence of heartbeats of the wearer for a period of time.

3. The electronic device of claim 1, wherein the processing element is further configured to generate a stream of electrocardiogram images, wherein the stream of electrocardiogram images corresponds to a plurality of heartbeats of the wearer, and wherein the processing element scrolls the electrocardiogram images on the display such that a most-recently generated electrocardiogram image is continuously presented on the display.

4. The electronic device of claim 1, wherein the processing element is in electronic communication with the location determining element and is configured to receive the determined geolocation of the electronic device from the location determining component.

5. The electronic device of claim 1, wherein the location determining component is further configured to utilize location determining signals received by the bezel when physical contact from the wearer's finger or thumb is not made with the bezel.

6. The electronic device of claim 1, wherein the processing element is further configured to control the plurality of electrical switches to selectively couple the bezel to the location determining component once physical contact is determined not to be made between the bezel and the wearer's finger or thumb.

7. The electronic device of claim 1, wherein the processing element is further configured to control the plurality of electrical switches to selectively couple the bezel to the processing element once physical contact is made between the bezel and the wearer's finger or thumb.

8. The electronic device of claim 7, wherein the processing element is further configured to:
  identify cardiovascular activity in a physical contact is made between the bezel and the wearer's finger or thumb based on the electrocardiogram signals received from the first contact point and the second contact point, and
  determine that physical contact is made between the bezel and the wearer's finger or thumb based on the identified cardiovascular activity.

9. The electronic device of claim 1, wherein the processing element comprises an electrocardiogram processing element that receives the electrocardiogram signals from the first and second contact points and generates the electrocardiogram waveform.

10. The electronic device of claim 1, wherein the electrocardiogram data comprises amplitudes corresponding to a QRS complex within the electrocardiogram waveform.

11. The electronic device of claim 1, wherein the optical assembly is configured to generate a photoplethysmogram (PPG) signal, and wherein the processing element is electrically coupled with the optical assembly and further configured to determine a heart rate of the wearer based on the PPG signal and present the determined heart rate on the display.

12. The electronic device of claim 1, wherein the plate includes an opening having a perimeter that encloses the optical assembly.

13. An electronic device configured to be worn on a wrist of a wearer, the electronic device comprising:
  a housing including a bottom surface;
  a bezel at least partially forming an antenna;
  a display at least partially surrounded by the bezel;
  a location determining element configured to receive location determining signals from the antenna and configured to determine a geolocation of the electronic device based on the received location determining signals;
  an optical assembly centrally-positioned on the bottom wall, the optical assembly including an optical transmitter configured to output light onto the wearer's wrist and an optical receiver configured to receive light reflected from the wearer's wrist;
  an electrically-conductive first contact point located on the bezel and positioned to be physically touched by a finger or thumb of the wearer;
  an electrically-conductive second contact point located on a plate on the bottom surface of the housing and configured to physically contact a wrist of the wearer when the electronic device is worn, the plate surrounding the optical assembly;
  a plurality of electrical switches; and
  a processing element electrically coupled with the plate, the bezel and the plurality of electrical switches, the processing element configured to—
    control the plurality of electrical switches to selectively coupling the bezel to the location determining component and the processing element,
    receive a first electrical bio signal from the first contact point once the bezel is physically touched by the finger or thumb of the wearer,
    receive a second electrical bio signal from the second contact point,
    generate an electrocardiogram waveform based on the first electrical bio signal and the second electrical bio signal, and
    graphically display the electrocardiogram waveform on the display.

14. The electronic device of claim 13, wherein the processing element is further configured to utilize electrocardiogram signals received through the bezel once physical contact is made with the bezel to generate the electrocardiogram waveform.

15. The electronic device of claim 13, wherein the electrocardiogram waveform is displayed as a sequence of single electrocardiogram images, with each electrocardiogram image corresponding to a heartbeat of the wearer.

16. The electronic device of claim 13, wherein the electrocardiogram waveform is displayed as a stream of electrocardiogram images, with each electrocardiogram image corresponding to a heartbeat of the wearer.

17. The electronic device of claim 13, wherein the optical assembly is configured to generate a photoplethysmogram (PPG) signal, and wherein the processing element is further configured to determine a heart rate of the wearer based on the PPG signal and present the determined heart rate on the display.

18. The electronic device of claim 13, wherein the processing element is in electronic communication with the location determining element and is configured to receive the determined geolocation of the electronic device from the location determining component.

19. The electronic device of claim 13, wherein the plate includes an opening having a perimeter that encloses the optical assembly.

20. The electronic device of claim 13, wherein the processing element is further configured to control the plurality of electrical switches to selectively couple the bezel to the location determining component once physical contact is determined not to be made between the bezel and the wearer's finger or thumb.

21. The electronic device of claim 13, wherein the processing element is further configured to control the plurality of electrical switches to selectively couple the bezel to the processing element once physical contact is made between the bezel and the wearer's finger or thumb.

22. An electronic device configured to be worn by a wearer during a physical activity, the electronic device comprising:
  a display;
  a housing including a bottom surface, a side wall having an opening and an electrically-conductive bezel at least partially forming an antenna;
  a location determining element configured to receive location determining signals from the antenna and configured to determine a geolocation of the electronic device based on the received location determining signals;

an optical assembly centrally-positioned on the bottom wall, the optical assembly including an optical transmitter configured to output light onto the wearer's wrist and an optical receiver configured to receive light reflected from the wearer's wrist;

an electrically-conductive pushbutton including a shaft passing through the opening of the sidewall and configured to be physically touched by a finger or thumb of the wearer, the pushbutton providing a first contact point;

an electrically-conductive second contact point located on a plate positioned on the bottom surface of the housing and configured to physically contact a wrist of the wearer when the electronic device is worn, the plate surrounding the optical assembly;

a plurality of electrical switches; and a processing element electrically coupled with the plate, the pushbutton and the plurality of electrical switches, the processing element configured to control the plurality of electrical switches to selectively coupling the bezel to the location determining component and the pushbutton to the processing element, receive a first electrical bio signal from the first contact point once the finger or thumb of the wearer contacts the pushbutton, receive a second electrical bio signal from the second contact point, generate an electrocardiogram waveform based on the first electrical bio signal and the second electrical bio signal, and graphically display the electrocardiogram waveform on the display.

23. The electronic device of claim 22, wherein the pushbutton is further configured to be depressible or rotatable to provide user inputs.

24. The electronic device of claim 22, wherein the electrocardiogram waveform is displayed as a sequence of single electrocardiogram images, with each electrocardiogram image corresponding to a heartbeat of the wearer.

25. The electronic device of claim 22, wherein the electrocardiogram waveform is displayed as a stream of electrocardiogram images, with each electrocardiogram image corresponding to a heartbeat of the wearer.

26. The electronic device of claim 22, wherein the optical assembly is configured to generate a photoplethysmogram (PPG) signal, and wherein the processing element is further configured to determine a heart rate of the wearer based on the PPG signal and present the determined heart rate on the display.

27. The electronic device of claim 22, wherein the processing element is in electronic communication with the location determining element and is configured to receive the determined geolocation of the electronic from the location determining component.

28. The electronic device of claim 22, wherein the plate includes an opening having a perimeter that encloses the optical assembly.

29. The electronic device of claim 22, wherein the processing element is further configured to control the plurality of electrical switches to selectively couple the bezel to the location determining component once physical contact is determined not to be made between the bezel and the wearer's finger or thumb.

30. The electronic device of claim 22, wherein the processing element is further configured to control the plurality of electrical switches to selectively couple the bezel to the processing element once physical contact is made between the bezel and the wearer's finger or thumb.

* * * * *